United States Patent [19]

Cooper et al.

[11] Patent Number: 5,214,044
[45] Date of Patent: May 25, 1993

[54] 1,4-DIHYDROPYRIDINES USEFUL AS PHARMACEUTICALS

[75] Inventors: Kelvin Cooper, Noank, Conn.; Michael J. Fray, Nr. Canterbury, England

[73] Assignee: Pfizer Inc., New York, N.Y.

[21] Appl. No.: 762,013

[22] PCT Filed: Feb. 22, 1990

[86] PCT No.: PCT/EP90/00336
§ 371 Date: Sep. 18, 1991
§ 102(e) Date: Sep. 18, 1991

[87] PCT Pub. No.: WO90/11280
PCT Pub. Date: Oct. 4, 1990

[30] Foreign Application Priority Data

Mar. 20, 1989 [GB] United Kingdom ............... 8906324

[51] Int. Cl.⁵ .................... A61K 31/44; C07D 471/04
[52] U.S. Cl. .................... 514/248; 514/249; 514/253; 514/256; 514/262; 514/266; 514/300; 514/303; 514/333; 544/236; 544/238; 544/254; 544/276; 544/277; 544/333; 544/350; 544/405; 546/117; 546/118; 546/256

[58] Field of Search .............. 546/118, 256, 117; 514/300, 303, 248, 249, 253, 256, 262, 266, 333; 544/236, 238, 254, 276, 277, 333, 350, 405

[56] References Cited

U.S. PATENT DOCUMENTS 4,801,598   1/1989   Cooper et al. ............... 514/333

*Primary Examiner*—Bernard Dentz
*Attorney, Agent, or Firm*—Peter C. Richardson; Gregg C. Benson; Robert T. Ronau

[57] ABSTRACT

The invention provides compounds of the formula:

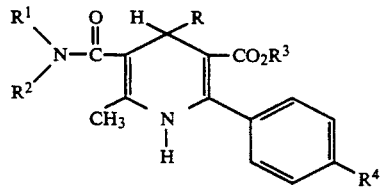

The variables are defined in the specification. The compounds are useful e.g. for the curative or prophylactic treatment of allergic conditions.

11 Claims, No Drawings

1,4-DIHYDROPYRIDINES USEFUL AS PHARMACEUTICALS

This application derives priority from PCT/EP 90/00336 filed Mar. 20, 1989 which now is International Publication Number WO 90/11280.

This invention relates to certain 4-heteroaryl-1,4-dihydropyridines. More particularly, this invention relates to certain 3-alkoxycarbonyl-4-heteroaryl-2-(4-heteroaryl)phenyl-6-methyl-1,4-dihydropyridine-5-carboxamide derivatives which are potent and selective antagonists of platelet activating factor (PAF) having clinical utility in the treatment of allergic, hypersecretory and inflammatory conditions in humans and animals.

Platelet activating factor (PAF: 1-0-alkyl-2-acetyl-snglyceryl-3-phosphorylcholine) is an ether phospholipid whose structure was first elucidated in 1979. It is produced by, released from and interacts with many pro-inflammatory cells, platelets and the kidney. In addition to potent platelet aggregating activity, PAF exhibits a wide spectrum of biological activities elicited either directly or via the release of other powerful mediators such as thromboxane $A_2$ or the leukotrienes. In vitro, PAF stimulates the movement and aggregation of neutrophils and the release therefrom of tissue-damaging enzymes and oxygen radicals. These activities contribute to actions of PAF in vivo consistent with it playing a significant role in inflammatory and allergic responses. Thus, intradermal PAF has been shown to induce an inflammatory response, with associated pain, accumulation of inflammatory cells and increased vascular permeability, comparable with the allergic skin reaction following exposure to allergen. Similarly, both the acute bronchoconstriction and chronic inflammatory reactions elicited by allergens in asthma can be mimicked by intratracheal administration of PAF. Accordingly agents which antagonise the actions of PAF and, consequently also prevent mediator release by PAF, will have clinical utility in the treatment of a variety of allergic, inflammatory and hypersecretory conditions such as asthma, arthritis, rhinitis, bronchitis and urticaria.

In addition to the above, PAF has been implicated as being involved in a number of other medical conditions. Thus in circulatory shock, which is characterised by systemic hypotension, pulmonary hypertension and increased lung vascular permeability, the symptoms can be mimicked by infusion of PAF. This, coupled with evidence showing that circulating PAF levels are increased by endotoxin infusion, indicates that PAF is a prime mediator in certain forms of shock. Intravenous infusion of PAF at doses of 20-200 pmol kg$^{-1}$ min$^{-1}$ into rats results in the formation of extensive haemorrhagic erosions in the gastric mucosa and thus PAF is the most potent gastric ulcerogen yet described whose endogenous release may underlie or contribute to certain forms of gastric ulceration. Psoriasis is an inflammatory and proliferative disease characterised by skin lesions. PAF is pro-inflammatory and has been isolated from lesioned scale of psoriatic patients indicating PAF has a role in the disease of psoriasis. Also increasing evidence supports a potential pathophysiological role for PAF in cardiovascular disease. Thus recent studies in angina patients show PAF is released during atrial pacing. Intracoronary injection of PAF in pigs induces a prolonged decrease in coronary flow and, in guinea pig hearts, it induces regional shunting and ischaemia. In addition PAF has been shown to initiate thrombus formation in a mesenteric artery preparation, both when administered exogenously and when released endogenously. More recently PAF has been shown to play a role in brain ischaemia induced in animal models of stroke.

Thus the compounds of the invention, by virtue of their ability to antagonise the actions of PAF, are of value in the treatment of the above conditions.

Our co-pending published patent applications EP-A-258033, EP-A-266989, EP-A-294074 and EP-A-310386 disclose 4-aryl-5-carbamoyl-1,4-dihydropyridines as PAF antagonists.

Thus the present invention provides compounds of the formula:

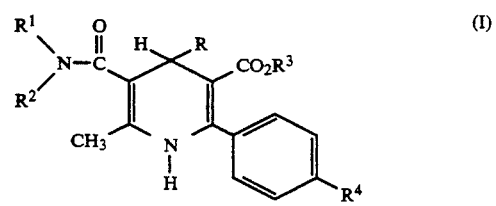

and the pharmaceutically acceptable salts thereof, wherein

R is a thienyl, benzothienyl, furyl, benzofuranyl, pyridinyl, quinolinyl or isoquinolinyl group, said groups being optionally substituted by up to 3 substituents each independently selected from nitro, halo, $C_1$-$C_4$ alkyl, $C_1$-$C_4$ alkoxy, aryl($C_1$-$C_4$)alkoxy, fluoro($C_1$-$C_4$)-alkoxy, $C_1$-$C_4$ alkylthio, $C_1$-$C_4$ alkanesulphonyl, hydroxy, trifluoromethyl and cyano; either $R^1$ and $R^2$ are each independently H or $C_1$-$C_6$ alkyl; or $R^1$ and $R^2$, taken together with the nitrogen atom to which they are attached, form a pyrrolidinyl, piperidinyl, morpholinyl, piperazinyl, N'-($C_1$-$C_4$ alkyl)piperazinyl or N'-($C_2$-$C_4$ alkanoyl)-piperazinyl group;

$R^1$ is H or $C_1$-$C_4$ alkyl and $R^2$ is cyano, $C_3$-$C_7$ cycloalkyl, aryl, heteroaryl or a $C_1$-$C_4$ alkyl group substituted by up to 2 substituents each independently selected from $C_3$-$C_7$ cycloalkyl, $C_1$-$C_4$ alkoxycarbonyl, aryl and heteroaryl;

$R^3$ is $C_1$-$C_6$ alkyl or aryl($C_1$-$C_4$)alkyl;

$R^4$ is either (a) an imidazolyl, triazolyl, pyridinyl, pyridazinyl, pyrimidinyl, pyrazinyl, oxazolyl or thiazolyl group, said group being optionally benzo-, pyrido-, pyridazino-, pyrimido- or pyrazino-fused, or (b) an oxazolo- or thiazolo-fused imidazolyl group, $R^4$ being optionally substituted by up to 3 substituents each independently selected from $C_1$-$C_4$ alkyl, $C_1$-$C_4$ alkoxy, trifluoromethyl, cyano and halo.

"Aryl", used in the definition of R, $R^2$ and $R^3$, is phenyl optionally substituted by up to 3 substituents each independently selected from halo, trifluoromethyl, $C_1$-$C_4$ alkyl, hydroxy, $C_1$-$C_4$ alkoxy, fluoro($C_1$-$C_4$)alkoxy, ($C_1$-$C_4$ alkoxy)carbonyl, $C_1$-$C_4$ alkanesulphonyl, sulphamoyl and cyano.

"Heteroaryl", used in the definition of $R^2$, is a 5- or 6-membered aromatic heterocyclic group containing up to 3 heteroatoms each selected from N, 0 and S and which may be optionally benzo-fused, said "heteroaryl" group being optionally substituted by up to 3 substituents each independently selected from $C_1$-$C_4$ alkyl, $C_1$-$C_4$ alkoxy and halo.

Examples of suitable "heteroaryl" groups include pyridinyl, thiazolyl, thiadiazolyl, oxazolyl, oxadiazolyl, isoxazolyl and imidazolyl, any of which may be optionally benzo-fused, said "heteroaryl" groups being optionally substituted by up to 3 substituents each independently selected from $C_1$-$C_4$ alkyl, $C_1$-$C_4$ alkoxy and halo.

Thus particular examples of $R^2$ as "heteroaryl" include pyridin-2-yl, 4- and 6-methylpyridin-2-yl, thiazol-2-yl, 4- and 5-methylthiazol-2-yl, 5-methyl-1,3,4-thiadiazol-2-yl, 5-methyl-1,2,4-oxadiazol-3-yl, 5-methylisoxazol-3-yl, benzothiazol-2-yl, 5-ethoxybenzothiazol-2-yl and 1-methylimidazol-2-yl.

"Halo" is fluoro, chloro, bromo or iodo.

Alkyl, alkanesulphonyl and alkoxy groups containing 3 or more carbon atoms, and $C_4$ alkanoyl groups, may be straight or branched chain.

The pharmaceutically acceptable acid addition salts of the compounds of formula (I) are those formed from acids which form non-toxic acid addition salts, for example the hydrochloride, hydrobromide, sulphate or bisulphate, phosphate, mono- or dihydrogen phosphate, acetate, citrate, fumarate, gluconate, lactate, maleate, succinate, tartrate, methanesulphonate, benzenesulphonate and p-toluenesulphonate.

Preferably, R is benzo[b]thien-3-yl, pyridin-2-yl, pyridin-3-yl, and 2-chloropyridin-3-yl.

Preferably $R^1$ is H and $R^2$ is H, $C_1$-$C_4$ alkyl, pyridinyl, thiazolyl or 1-(phenyl)ethyl.

Most preferably $R^1$ is H and $R^2$ is pyridin-2-yl.

Preferably, $R^3$ is methyl, ethyl or benzyl ring-substituted by up to 2 halo substituents.

Most preferably, $R^3$ is ethyl.

Preferably, $R^4$ is 2-methylimidazo[4,5-c]pyridin-1-yl, imidazol-1-yl, benzimidazol-1-yl, 2-methylbenzimidazol-1-yl, 3,5-dimethyl-1,2,4-triazol-4-yl, 2-trifluoromethylimidazo[4,5-c]pyridin-1-yl, 2-n-butylimidazo[4,5-c]pyridin-1-yl, 2-methylimidazo[4,5-b]pyridin-3-yl, 2-methylimidazo[1,2-a]pyridin-3-yl, 2-ethylimidazo[4,5-c]pyridin-1-yl, 7-methoxy-2-methylimidazo[4,5-d]pyrimidin-3-yl, 2-methylimidazo[4,5-c]-pyridin-3-yl, 2,4,6-trimethylimidazo[4,5-c]pyridin-1-yl, 2,4-dimethylimidazol-1-yl, 2-methylimidazol-1-yl, 2,4,5-trimethylimidazol-1-yl, 2,4-dimethyloxazol-5-yl, 2-methylimidazo[4,5-b]pyridin-1-yl, 4-methylimidazol-1-yl, 2-methylpyridin-3-yl, 2,6-dimethylpyridin-3-yl, 3,5-dimethyl-1,2,4-triazol-1-yl, 4-methyloxazol-5-yl, 2,4-dimethylthiazol-5-yl, 6-methylimidazo[2,1-b]thiazol-5-yl, or 4-methylthiazol-5-yl.

More preferably, $R^4$ is 2-methylimidazo[4,5-c]pyridin-1-yl or 2,4,6-trimethylimidazo[4,5-c]pyridin-1-yl.

Most preferably, $R^4$ is 2-methylimidazo[4,5-c]pyridin-1-yl.

A preferred individual compound is 4-(benzo[b]thien-3-yl)-1,4-dihydro-3-ethoxycarbonyl-6-methyl-2-[4-(2-methylimidazo[4,5-c]pyridin-1-yl)phenyl]-5-[N-(pyridin-2-yl)carbamoyl]pyridine.

The compounds of formula (I) contain at least one asymmetric centre and will therefore exist as one or more pairs of enantiomers, and such individual enantiomers or individual pair of enantiomers may be separable by physical methods, e.g. by fractional crystallisation or chromatography of the parent compounds or of a suitable salt or derivative thereof. The invention includes all the enantiomers of the compounds of formula (I) whether separated or not.

The compounds of the invention of formula (I) may be prepared according to the Hantzsch synthesis as illustrated by the following reaction scheme:

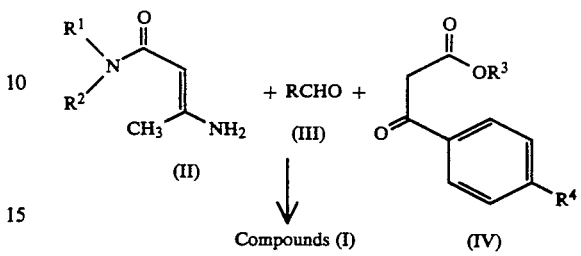

Compounds (I)

wherein R, $R^1$, $R^2$, $R^3$ and $R^4$ are as defined for formula (I).

In a typical procedure, the ketoester (IV) and the aldehyde (III) are heated together under reflux, preferably under a nitrogen atmosphere, in a suitable organic solvent, e.g. a $C_1$-$C_4$ alkanol such as ethanol, for about 15 minutes and then the 3-aminocrotonamide (II) is added. Alternatively, the mixture of the 3-aminocrotonamide (II), the ketoester (IV) and the aldehyde (III) can be heated together in the solvent. Optionally a small amount of a lower alkanoic acid, such as acetic acid, is added to neutralise the solution. The resulting solution can then be heated at from 50° to 130° C., preferably under reflux, until the reaction is essentially complete, typically in 24 hours or less. The product of the formula (I) can then be isolated and purified by conventional procedures, for example by partition, recrystallisation or by chromatography.

Alternatively, in a modification of the above procedure, the ketoester (IV) and the aldehyde (III) are first reacted together, typically by stirring a slight excess of the ketoester with the aldehyde at room temperature in a suitable organic solvent, e.g. isopropyl alcohol, optionally containing piperidine as a catalyst, to give an intermediate compound of formula (V):

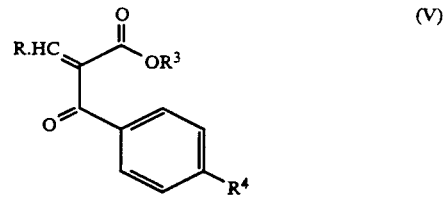

wherein R, $R^3$ and $R^4$ are as defined for formula (I).

If desired, the intermediate compound (V) may be separated, for example by evaporating the reaction mixture to produce an oil, triturating the oil with water, and purifying the solid product obtained by filtration and recrystallisation The compound of formula (V) may then be reacted with the 3-aminocrotonamide (II), typically by heating the compounds together at from 50° to 130° C., preferably under reflux, in a suitable organic solvent, e.g. a $C_1$-$C_4$ alkanol, and preferably under a nitrogen atmosphere, to produce the compound of the formula (I) which again can be isolated and purified by conventional methods.

The ketoesters (IV) are either known compounds or can be prepared by the following methods:

(i) The ketoesters (IV) may be prepared by a Blaise reaction based on a modification of the literature method according to S.M. Hannick, Y. Kishi, J. Org. Chem., 48, 3833, (1983), as illustrated by the following reaction sequence:

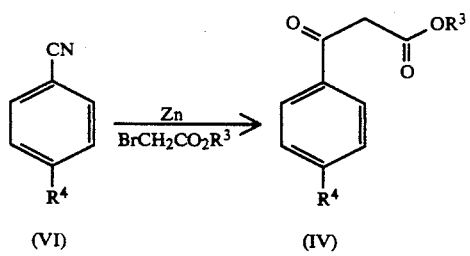

wherein $R^3$ and $R^4$ are as defined for formula (I).

In a typical procedure, the benzonitrile derivative (VI) is added to a suspension of zinc dust and a few drops of the appropriate bromoacetate in a suitable dry organic solvent, such as tetrahydrofuran, under a nitrogen atmosphere. The mixture is heated under reflux to initiate the reaction and further aliquots of the bromoacetate are then added. On completion of the reaction and after cooling, aqueous potassium carbonate is added. After filtration, the filtrate is treated with dilute hydrochloric acid or with 20% aqueous trifluoroacetic acid, together with a suitable solvent such as dichloromethane. The reaction mixture is then neutralised and the ketoester (IV) isolated and purified by conventional procedures.

The benzonitrile derivatives (VI) are either known compounds or may be prepared by conventional methods in accordance with literature precedents.

(ii) An alternative method for preparing certain ketoesters (IV) is illustrated by the following reaction sequence:

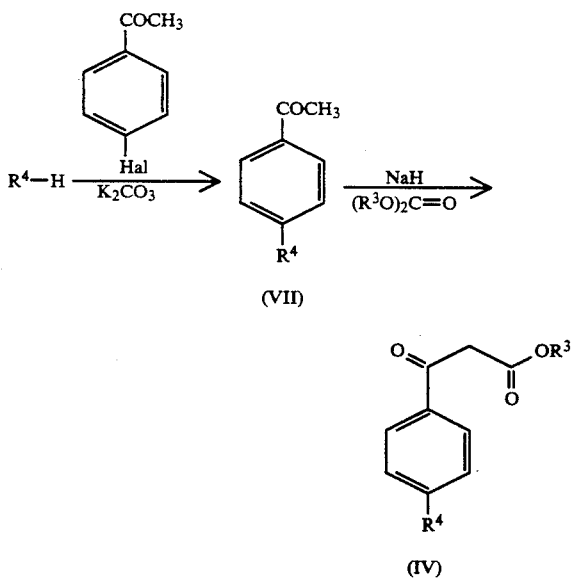

wherein "Hal" is halo preferably fluozo or bzomo, with the proviso that the hydrogen atom in $R^4$-H is attached to a ring nitrogen atom in $R^4$. Optionally, a copper/cuprous bromide catalyst may be added in the first stage of this sequence but this is usually unnecessary where "Hal" is fluoro.

In a typical procedure, a mixture of the compound of the formula $R^4$-H, p-bromoacetophenone, copper bronze, cuprous bromide and anhydrous potassium carbonate in a suitable solvent such as dry N-methylpyrrolidinone, is heated at about 150° C. under an atmosphere of dry nitrogen The intermediate ketone (VII) obtained is isolated and purified by conventional procedures, and is then added to a suspension of sodium hydride in a suitable dry solvent, such as tetrahydrofuran, under a nitrogen atmosphere. The appropriate dialkyl carbonate is added and the resultant mixture stirred at from 20° C. to reflux for a suitable period of time. Alternatively, the dialkyl carbonate may itself be used as the solvent. The ketoester (IV) obtained is isolated and purified by conventional procedures.

The aldehydes of the formula (III) and the 3-aminocrotonamide derivatives (II) are either known compounds or can be prepared by conventional methods in accordance with literature precedents.

All of the above reactions are conventional and appropriate reagents and reaction conditions for their performance and procedures for isolating the desired products will be well known to those skilled in the art, in accordance with literature precedents and by reference to the following Examples and Preparations.

Pharmaceutically acceptable salts are readily prepared by mixing solutions containing equimolar amounts of the free base and the desired acid. The salt generally precipitates from solution and is collected by filtration, or is recovered by evaporation of the solvent.

The activity of the compounds of the formula (I) is shown by their ability to inhibit the platelet aggregating activity of PAF in vitro. Testing is performed as follows:

Blood samples are taken from either rabbit or man into 0.1 vol disodium ethylenediaminetetraacetic acid buffer and the samples centrifuged for 15 minutes to obtain platelet rich plasma. The plasma is further centrifuged to give a platelet pellet which is washed with a buffer solution (4 mM $KH_2PO_4$, 6 mM $Na_2HPO_4$, 100 mM NaCl, 0.1% glucose and 0.1% bovine serum albumin, pH 7.25) and finally resuspended in buffer solution to a concentration of $2 \times 10^8$ platelets/ml. A sample (0.5 ml) is pre-incubated for two minutes at 37° C. in a Paton aggregometer with stirring, either with vehicle alone, or with vehicle containing the particular compound under test. PAF is added at a sufficient concentration to give a maximum aggregating response in the absence of test compound ($10^{-8}$ to $10^{-9}$ molar), and the platelet aggregation is measured by following the increase in light transmission of the solution The experiment is repeated in the presence of test compound at a range of concentrations and the concentration of compound required to reduce the response to 50% of its maximum value is recorded as the $IC_{50}$ value.

The activity of the compounds of formula (I) is also demonstrated in vivo by their ability to protect mice from the lethal effect of an injection of PAF. A mixture of PAF (50 ug/kg) and DL-propranolol (5 mg/kg) in 0.9% w/v sodium chloride is injected (0.2 ml) via a tail vein into mice. The compounds under test are either injected into the tail vein immediately prior to the PAF/propranolol injection, or administered orally by gavage two hours earlier. The compounds are tested at several doses in groups of 5 mice and the dose which reduces mortality to 50% is recorded as the $PD_{50}$ value.

The compounds are also tested for their ability to reduce PAF-induced bronchoconstriction in anaesthetised guinea pigs In this test, airways resistance and dynamic lung compliance are calculated from recordings of airflow and transpleural pressure and calculation of tidal volume. The bronchoconstriction induced by PAF (100 ng/kg) is determined. One hour after the initial dose of PAF, the compound under test is administered and the PAF challenge repeated. The ability of the compound to reduce the bronchoconstrictor effect of PAF is recorded as a ratio.

For therapeutic use the compounds of the formula (I) will generally be administered in admixture with a pharmaceutical carrier selected with regard to the intended route of administration and standard pharmaceutical practice. For example, they may be administered orally in the form of tablets containing such excipients as starch or lactose, or in capsules or ovules either alone or in admixture with excipients, or in the form of elixirs or suspensions containing flavouring or colouring agents. They may be injected parenterally, for example, intravenously, intramuscularly or subcutaneously. For parenteral administration, they are best used in the form of a sterile aqueous solution which may contain other substances, for example, enough salts or glucose to make the solution isotonic with blood.

For administration to man in the curative or prophylactic treatment of allergic bronchial conditions and arthritis, oral dosages of the compounds will generally be in the range of from 2-1000 mg daily for an average adult patient (70 kg). Thus for a typical adult patient, individual tablets or capsules contain from 1 to 500 mg of active compound, in a suitable pharmaceutically acceptable vehicle or carrier. Dosages for intravenous administration would typically be within the range from 1 to 10 mg per single dose as required for the treatment of allergic and bronchial hyper-reactive conditions, inhalation via a nebuliser or aerosol may be the preferred route of drug administration. Dose levels by this route would be within the range from 0.1 to 50 mg per single dose as required In practice the physician will determine the actual dosage which will be most suitable for an individual patient and it will vary with the age, weight and response of the particular patient. The above dosages are exemplary of the average case but there can, of course, be individual instances where higher or lower dosage ranges are merited, and such are within the scope of this invention.

Thus, in a further aspect, the invention provides a pharmaceutical composition comprising a compound of the formula (I), or a pharmaceutically acceptable salt thereof, together with a pharmaceutically acceptable diluent or carrier.

The invention also includes a compound of the formula (I), or a pharmaceutically acceptable salt or composition thereof, for use as a medicament.

The invention further provides the use of a compound of the formula (I), or of a pharmaceutically acceptable salt or composition thereof, for the manufacture of a medicament for the treatment of allergic, hypersecretory and inflammatory conditions.

The invention yet further provides a method of treating an animal (including a human being) to cure or prevent allergic, hypersecretory and inflammatory conditions, which comprises administering to said animal or human being, a therapeutically effective amount of a compound of the formula (I), or a pharmaceutically acceptable salt or composition thereof.

The preparation of the compounds of the invention is further illustrated by the following Examples:

EXAMPLE 1

4-(Benzo[b]thien-3-yl)-1,4-dihydro-3-ethoxycarbonyl-6-methyl-2-[4-(2-methylimidazo[4,5-c]pyridin-1-yl)nhenyl]-5-[N-(Pyridin-2-yl)carbamoyl]pnyridine

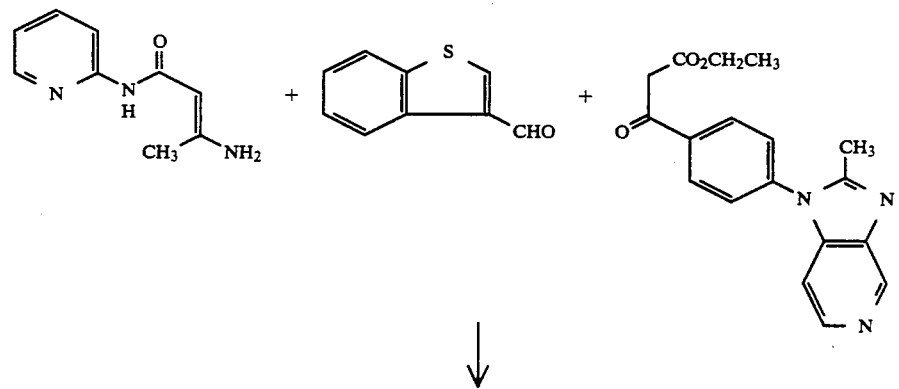

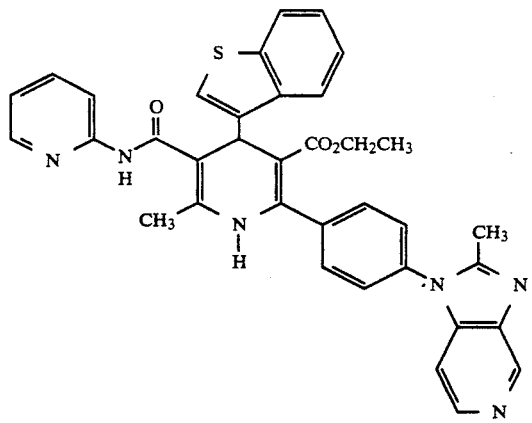

A mixture of ethyl 4'-(2-methylimidazo[4,5-c]pyridin-1-yl)benzoylacetate (see Preparation 1) (646 mg, 2 mmol), 3-amino-N-(pyridin-2-yl)crotonamide (353 mg, 2 mmol) and benzo[b]thiophene-3-carboxaldehyde (324 mg, 2 mmol) in absolute ethanol was heated under a nitrogen atmosphere under reflux for 6 hours. The solution was allowed to cool and the solvent was removed under reduced pressure The residue was purified by flash chromatography (gradient elution with ethyl acetate changing to 7% diethylamine/ethyl acetate) and the fractions containing the product were combined and concentrated. The solid product obtained was triturated with ether/ethyl acetate and then filtered to give the title compound as a colourless solid (250 mg, 20%), m.p. 230°–238° C.

Analysis %:
Found: C, 68.14; H, 4.79; N, 13.17:
Calculated for $C_{36}H_{30}N_6O_3S \cdot \frac{1}{2}H_2O$: C, 67.96; H, 4.87; N, 13.21.

EXAMPLES 2 to 4

The following tabulated examples of general formula:

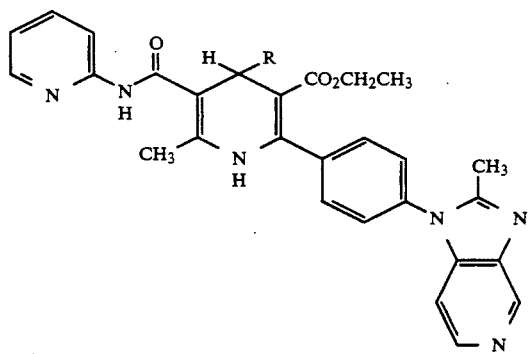

were prepared using similar conditions to those described for Example 1 using the appropriate heteroaromatic aldehyde, 3-aminocrotonamide and ketoester derivatives.

| Example No. | R | m.p. (°C.) | Analysis (%) |
|---|---|---|---|
| 2 | (pyridin-2-yl) | 240–250 | Found: C,67.87; H,5.09; N,16.79; Calculated for $C_{33}H_{29}N_7O_3 \cdot 0.5\ H_2O$: C,68.26; H,5.21; N,16.89. |
| 3 | (pyridin-3-yl) | 210–215 | Found: C,66.63; H,5.01; N,16.66; Calculated for $C_{33}H_{29}N_7O_3 \cdot 1.25\ H_2O$: C,66.65; H,5.30; N,16.50. |
| 4 | (2-chloropyridin-3-yl) | 235–245 | Found: C,64.62; H,4.79; N,15.69; Calculated for $C_{33}H_{28}ClN_7O_3 \cdot 0.5\ H_2O$: C,64.44; H,4.75; N,15.94. |

The following Preparation illustrates the preparation of the ketoester used in the preceding Examples:

Preparation 1

Ethyl 4'-(2-methylimidazo[4,5-c]pyridin-1-yl)benzoylacetate

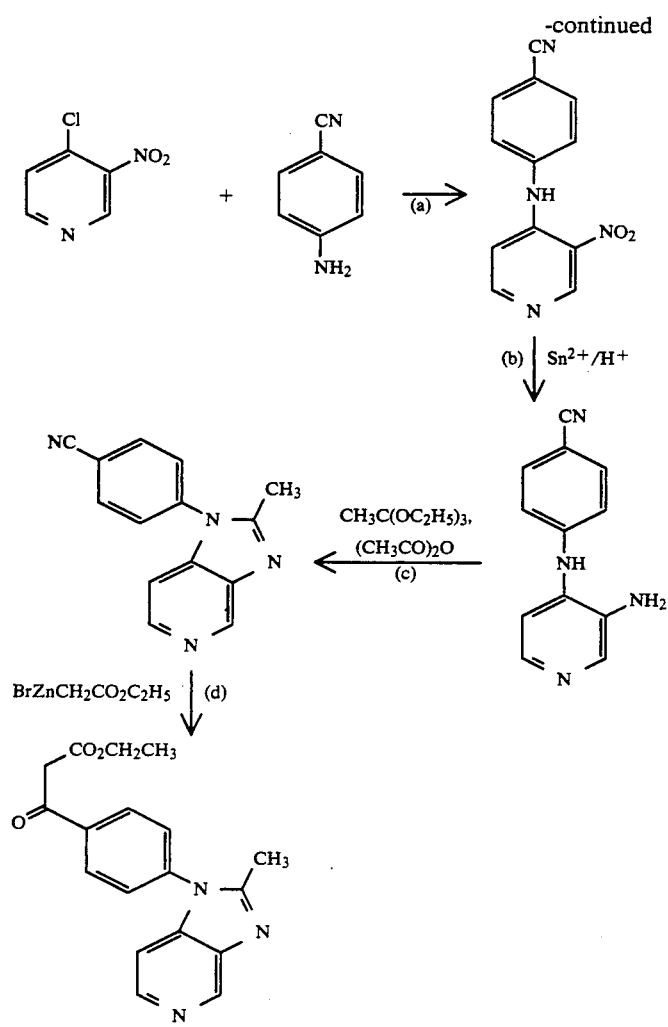

(a) 4-[N-(4-Cyanophenyl)amino]-3-nitropyridine

According to the method of J.C.S. Perkin Trans. I, 1979, 135, p-cyanoaniline (6 894 g, 58.4 mmol) was added to a solution of 4-chloro-3-nitropyridine (9.26 g, 58.4 mmol) in ethanol (200 ml) and the mixture was stirred at room temperature for 18 hours. The resulting yellow suspension was poured into 500 ml of ice-cold dilute ammonia and filtered The solid was treated with 150 ml of boiling ethanol, cooled in ice, and filtered to give the title compound as a bright yellow powder, (12.15 g), m.p. 210°–211° C.

$^1$H-NMR (CDCl$_3$): δ=7.15 (1H, d, J=6 Hz), 7.45 (2H, d, J=9 Hz), 7.79 (2H, d, J=9 Hz), 8.43 (1H, d, J=6 Hz), 9.36 (1H, s), 9.80 (1H, br, s) p.p.m.

(b) 3-Amino-4-[N-(4-cyanophenyl)amino]pyridine

According to a modification of the method of Pharm. Helv. Acta, 50, 188 (1975), tin(II) dichloride dihydrate (56.4 g, 250 mmol) was added to a suspension of 4-[N-(4-cyanophenyl)amino]-3-nitropyridine (see part (a)) (12.0 g, 50 mmol) in 2N aqueous hydrochloric acid (35 ml), water (150 ml) and ethanol (75 ml) and the resulting mixture was heated under reflux for 10 minutes under nitrogen. The mixture was cooled in ice, poured into ice-cold 2N aqueous sodium hydroxide (400 ml) and filtered The creamy-coloured solid was washed with 2N aqueous sodium hydroxide and water, and then dried in a vacuum desiccator to provide the title compound, (9.31 g), which gradually turns reddish brown on exposure to light and air.

$^1$H-NMR (CDCl$_3$): δ=3.52 (2H, br s), 6.04 (1H, br s), 7.03 (2H, d, J=9 Hz), 7.59 (2H, d, J=9 Hz), 8.07 (1H, m), 8.20 (1H, s) p.p.m.

(c) 1-(4-Cyanophenyl)-2-methylimidazo[4,5-c]pyridine

A mixture of 3-amino-4-[N-(4-cyanophenyl)amino]-pyridine (see part (b)) (9.31 g, 44.3 mmol), triethyl orthoacetate (40 ml) and acetic anhydride (30 ml) was heated under reflux for 2 hours under nitrogen, cooled, then concentrated under reduced pressure The brown residue was dissolved in 1M hydrochloric acid and washed with ethyl acetate (200 ml). The aqueous layer was rendered basic with saturated aqueous ammonia and extracted with dichloromethane (3×200 ml). The combined extracts were washed with water, dried (MgSO$_4$) and concentrated to give the title compound (6.5 g), as a brown solid.

$^1$H-NMR (CDCl$_3$): δ=2.61 (3H, s), 7.13 (1H, d, J=6 Hz), 7.58 (2H, d, J=9 Hz), 7.98 (2H, d, J=9 Hz), 8.45 (1H, d, J=6 Hz), 9.11 (1H, s) p.p.m.

(d) Ethyl 4'-(2-methylimidazo[4,5-c]pyridin-1-yl)benzoylacetate

Zinc dust (894 mg, 13.7 mmol) was suspended in dry THF (3 ml) under nitrogen and sonicated at room temperature for 10 minutes. Ethyl bromoacetate (2 drops) was added and the mixture was heated under reflux for 5 minutes. A solution of 1-(4-cyanophenyl)-2-methylimidazo[4,5-c]pyridine (640 mg, 2.74 mmol) in dry THF (6 ml) was added and the mixture was refluxed for 5 minutes. A solution of ethyl bromoacetate (1.822 g, 10.94 mmol) in dry THF (2 ml) was added dropwise over 1 hour at reflux and, after a further 10 minutes, the mixture was allowed to cool to room temperature. 50% aqueous potassium carbonate (1 ml) was added and the mixture was stirred for 45 minutes at room temperature then filtered through "Arbocel" (Trade Mark), a cellulose based filter aid, washing with THF. The filtrate was concentrated under reduced pressure to give a yellow gum. This material was treated with a mixture of 20% aqueous trifluoroacetic acid (10 ml) and dichloromethane (50 ml) and stirred at room temperature for 15 minutes. The mixture was neutralised by the addition of saturated aqueous sodium bicarbonate and then extracted with dichloromethane (2×30 ml). The combined extracts were dried (MgSO$_4$), concentrated under reduced pressure and the crude product was purified by flash chromatography on silica gel (eluting with 10% changing to 20% methanol/ethyl acetate) to give, after combination and evaporation of appropriate fractions, the title compound (480 mg, 54%), as a yellow gum. This material was rechromatographed (eluting with 7:1 ethyl acetate/methanol) to give, after combination and evaporation of appropriate fractions, a white solid, m.p. 111°–112° C. (ethyl acetate).

$^1$H-NMR (CDCl$_3$): δ=1.32 ((3H, t, J=6 Hz), 2.61 (3H, s), 4.09 (2H, s), 4.28 (2H, q, J=6 Hz), 7.16 (1H, d, J=6 Hz), 7.55 (2H, d, J=9 Hz), 8.23 (2H, d, J=9 Hz), 8.46 (1H, d, J=6 Hz), 9.09 (1H, s) p.p.m.

We claim:

1. A compound of the formula

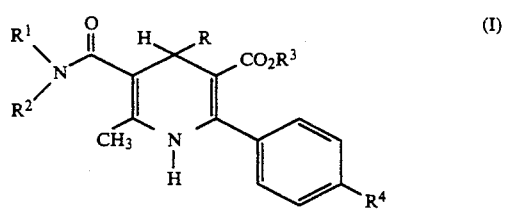

or a pharmaceutically acceptable salt thereof, wherein:
R is a thienyl, benzothienyl, furyl or benzofuranyl group, said group being optionally substituted by up to three substituents each independently selected from the group consisting of nitro, halo, (C$_1$–C$_4$)alkyl, (C$_1$–C$_4$)alkoxy, hydroxy, aryl(-C$_1$–C$_4$)alkoxy, fluoro (C$_1$–C$_4$)alkoxy, (C$_1$–C$_4$)alkylthio, (C$_1$–C$_4$)alkanesulphonyl, trifluoromethyl and cyano;
R$^1$ is hydrogen or (C$_1$–C$_4$)alkyl;
R$^2$ is pyridyl, pyrimidinyl, pyridazinyl or pyrazinyl;
R$^3$ is (C$_1$–C$_4$)alkyl or aryl(C$_1$–C$_4$)alkyl; and
R$^4$ is an imidazolyl or triazolyl group, said group being optionally benzo-, pyrido-, pyridazino-, pyrimido- or pyrazino-fused and optionally substituted by up to three substituents each independently selected from the group consisting of (C$_1$–C$_4$)alkyl, (C$_1$–C$_4$)alkoxy, trifluoromethyl and halo.

2. A compound according to claim 1 wherein R$^2$ is pyridyl.

3. A compound according to claim 2 wherein R is benzothien-3-yl.

4. A compound according to claim 3 wherein R$^1$ is hydrogen.

5. A compound according to claim 4 wherein R$^2$ is pyridin-2-yl.

6. A compound according to claim 5 wherein R$^3$ is methyl, ethyl or benzyl.

7. A compound according to claim 6 wherein R$^3$ is ethyl.

8. A compound according to claim 7 wherein R$^4$ is 2-methylimidazo[4,5-c]pyridin-1-yl or 2,4,6-trimethylimidazo[4,5-c]pyridin-1-yl.

9. The compound according to claim 8 wherein R$^4$ is 2-methylimidazo[4,5-c]pyridin-1-yl.

10. A pharmaceutical composition comprising a hypoallergenic amount of a compound according to claim 1 and a pharmaceutically acceptable carrier or diluent.

11. A method of treating allergies in a mammal in need of such treatment comprising administering to said mammal a hypoallergenic amount of a compound according to claim 1.

* * * * *